US012584087B2

(12) United States Patent
Desanti et al.

(10) Patent No.: US 12,584,087 B2
(45) Date of Patent: Mar. 24, 2026

(54) BIOLOGICAL CULTURE UNIT

(71) Applicant: Battelle Memorial Institute, Columbus, OH (US)

(72) Inventors: Charles L. Desanti, Columbus, OH (US); Ryan W. Daly, Columbus, OH (US); David Charles Seibert, Jr., Columbus, OH (US); Patrick Norris, Columbus, OH (US); John Bartholomew, Columbus, OH (US); Sherry K. Blight, Columbus, OH (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 113 days.

(21) Appl. No.: 18/625,358

(22) Filed: Apr. 3, 2024

(65) Prior Publication Data

US 2024/0271072 A1     Aug. 15, 2024

Related U.S. Application Data

(63) Continuation of application No. 17/002,940, filed on Aug. 26, 2020, now Pat. No. 11,976,262.

(Continued)

(51) Int. Cl.
| | |
|---|---|
| *C12M 1/00* | (2006.01) |
| *C12M 1/34* | (2006.01) |
| *C12M 3/06* | (2006.01) |

(52) U.S. Cl.
CPC ............ *C12M 23/16* (2013.01); *C12M 23/34* (2013.01); *C12M 23/40* (2013.01); *C12M 27/18* (2013.01); *C12M 29/10* (2013.01); *C12M 41/46* (2013.01)

(58) Field of Classification Search
CPC ...... C12M 23/16; C12M 23/34; C12M 23/40; C12M 27/18; C12M 29/10; C12M 41/46; C12M 23/38; C12M 37/04; C12M 23/08
See application file for complete search history.

(56) References Cited

U.S. PATENT DOCUMENTS

| | | | |
|---|---|---|---|
| 2011/0244466 A1* | 10/2011 | Juncosa | ............ B01L 3/502715 |
| | | | 435/6.12 |
| 2018/0251722 A1* | 9/2018 | Patil | ....................... C12M 41/48 |

FOREIGN PATENT DOCUMENTS

| WO | WO 2007/070740 A2 | 6/2007 |
|---|---|---|
| WO | WO 2019/140532 A1 | 7/2019 |

OTHER PUBLICATIONS

Rountree et al., "BaroFuse, a novel pressure-driven, adjustable-throughput perfusion system for tissue maintenance and assessment," 1-18, 2016).*

(Continued)

*Primary Examiner* — Liban M Hassan
(74) *Attorney, Agent, or Firm* — Lippes Mathias LLP

(57)     ABSTRACT

A biological culture unit comprises a chamber body and a valve plate. The chamber body has defined therein a growth chamber and an aliquot chamber. The valve plate is disposed on the top surface of the chamber body and is movable to define selectable configurations of the biological culture unit for: (1) loading the growth chamber; (3) transferring an aliquot from the growth chamber to the aliquot chamber via a path defined within the biological culture unit in the transfer position; and (4) extracting the aliquot from the aliquot chamber. The selectable positions may further include (2) a growth position, and (5) a termination position for putting a termination agent into the growth and aliquot chambers. The valve plate may further include a neutralizer port that is aligned with the aliquot chamber in the loading (Continued)

position, for loading a neutralizing agent into the aliquot chamber.

20 Claims, 9 Drawing Sheets

Related U.S. Application Data

(60)   Provisional application No. 62/892,321, filed on Aug. 27, 2019.

(56)                    References Cited

OTHER PUBLICATIONS

International Search Report dated Dec. 10, 2020 in PCT/US2020/047863.

* cited by examiner

Extraction Position #4

Transfer Position #3

Transfer Position #3

Extraction Position #4

Growth Position #2
And
Termination Position #5

BIOLOGICAL CULTURE UNIT

CROSS-REFERENCE TO RELATED APPLICATIONS

This application is a continuation of U.S. patent application Ser. No. 17/002,940, filed Aug. 26, 2020, now U.S. patent No. //fill in later//, which claims priority to U.S. Provisional Patent Application Ser. No. 62/892,321, filed on Aug. 27, 2019, which is incorporated by reference in its entirety.

STATEMENT REGARDING FEDERALLY SPONSORED RESEARCH OR DEVELOPMENT

This invention was made with government support under (HDTRA1-14-D-0002-0004) awarded by the Defense Threat Reduction Agency (DTRA). The government has certain rights in the invention.

BACKGROUND

The following relates to the biological culturing arts, biological hazard response arts, and the like.

In tasks such as tracking an outbreak of an infectious disease, or assessing a possible site of biological hazard contamination, it is known to take samples of the possible biological agent. For example, an oral swab may be taken from a person suspected of being infected by an outbreak disease, or surfaces of a possibly contaminated site may be similarly swabbed. The amount of biological agent contained in such a swab or other sample may, however, be low. To improved detectability of the suspected hazardous biological agent, it is known to perform biological amplification by growing a culture from the sample. While this substantially improves detectability (by orders of magnitude in most cases), the biological amplification carries a concomitantly amplified risk of inadvertent transmission of the hazardous biological agent (if present) to medical personnel, biologically hazardous material (biohazmat) workers, or other persons performing the sampling or in the immediate vicinity. Fortunately, effective systems and procedures have been developed for safely handing potentially hazardous biological cultures at advanced laboratories such as those maintained by the Centers for Disease Control (CDC) and the like.

However, the ability to safely grow a potentially hazardous biological culture in the field is much more difficult. An austere environment such as a mobile biological laboratory deployed at the site of a medical disease outbreak or possible biohazard contamination site typically does not have sophisticated laboratory equipment sufficient to safely grow a culture on-site. Due to the exponentially magnified risk involved with microbiological culturing activities, samples are usually tested on-site without culturing. But this approach sacrifices the enhanced detectability provided by biological amplification. Additionally or alternatively, samples may be shipped to the CDC or another advanced laboratory at which the culture can be more safely grown, but this delays receiving the results and introduces sample transportation safety concerns. Moreover, this approach increases the (often already heavy) workload on the advanced laboratory.

Certain improvements are disclosed herein.

BRIEF SUMMARY

In accordance with some illustrative embodiments disclosed herein, a biological culture unit is disclosed. A chamber body has a top surface and a bottom surface. The chamber body has defined therein a growth chamber having an access opening at the top surface, and an aliquot chamber having an access opening at the top surface. A first fluid path extends from the growth chamber to the top surface, and a second fluid path extends from the aliquot chamber to the top surface. The biological culture unit further includes a valve plate disposed on the top surface of the chamber body and rotatably connected with the chamber body to rotate about a rotation axis relative to the chamber body. The valve plate includes a growth chamber access port, an aliquot chamber access port, a transfer actuator, and a third fluid path. The valve plate is rotatable about the rotation axis into a plurality of selectable positions including: a loading position in which the growth chamber access port is aligned with the access opening of the growth chamber and the third fluid path is not aligned to connect the first and second fluid paths; a transfer position in which the third fluid path is aligned to connect the first and second fluid paths and the transfer actuator is aligned with one of the access opening of the growth chamber and the access opening of the aliquot chamber; and an extraction position in which the aliquot chamber access port is aligned with the access opening of the aliquot chamber and the third fluid path is not aligned to connect the first and second fluid paths. In some embodiments, the valve plate further includes a neutralizer port which is aligned with the aliquot chamber when the valve plate is rotated into the loading position. In some embodiments, rotation of the valve plate in a sequence rotary direction cycles through the loading position, the transfer position, and the extraction position in that order. In some embodiments, the plurality of selectable positions further includes a growth position in which the chamber access port is not aligned with the access opening of the growth chamber and the third fluid path is not aligned to connect the first and second fluid paths and the aliquot chamber access port is not aligned with the access opening of the aliquot chamber. In some embodiments, the valve plate further includes first and second terminator ports, and the plurality of selectable positions further includes a termination position in which the first terminator port is aligned with the access opening of the growth chamber and the second terminator port is aligned with the access opening of the aliquot chamber. In some embodiments, the transfer actuator comprises a gas coupling. In some embodiments, the transfer actuator comprises a plunger that is operable when the valve plate is in the transfer position to increase pressure in the growth chamber. In some embodiments the chamber body comprises a transparent or translucent material. In some embodiments the bottom surface of the chamber body has formed therein a growth chamber heater post receptacle aligned with the growth chamber and an aliquot chamber heater post receptacle aligned with the aliquot chamber.

In accordance with some illustrative embodiments disclosed herein, a method of biological culture is performed in conjunction with the biological culture unit of the immediately preceding paragraph. With the valve plate in the loading position, a biological sample and a growth medium are loaded into the growth chamber via the growth chamber access port aligned with the access opening of the growth chamber. After the loading, a period of microbiological growth is caused to occur, after which an aliquot is transferred into the aliquot chamber by rotating the valve plate to the transfer position and, with the valve plate in the transfer position, operating the transfer actuator to transfer the aliquot from the growth chamber to the aliquot chamber via a transfer route defined by the first fluid path and the second fluid path connected by the third fluid path. After the transferring, the aliquot is extracted by rotating the valve plate to the extraction position and, with the valve plate in the extraction position, removing the aliquot from the aliquot chamber via the aliquot chamber access port aligned with the access opening of the aliquot chamber. In some embodiments, the method further includes, after the transferring and before the extracting, heating the aliquot chamber.

In accordance with some illustrative embodiments disclosed herein, a biological culture unit comprises: a chamber body having a top surface and a bottom surface, the chamber body having defined therein a growth chamber having an access opening at the top surface and an aliquot chamber having an access opening at the top surface and a first fluid path extending from the growth chamber to the top surface and a second fluid path extending from the aliquot chamber to the top surface; and a valve plate disposed on the top surface of the chamber body and movable to define selectable configurations of the biological culture unit. The selectable configurations include: a loading configuration in which the growth chamber is accessible via the access opening of the growth chamber and the first and second fluid paths are not connected together; a transfer configuration in which the access opening of the growth chamber is sealed by the valve plate, the access opening of the aliquot chamber is sealed by the valve plate, and the first and second fluid paths are connected together by a third fluid path defined in the valve plate; and an extraction position in which the aliquot chamber is accessible via the access opening of the aliquot chamber, access opening of the growth chamber is sealed by the valve plate, and the first and second fluid paths are not connected together.

In accordance with some illustrative embodiments disclosed herein, a biological culture unit comprises: a chamber body having defined therein a growth chamber and an aliquot chamber; and a valve plate disposed on a top surface of the chamber body and movable to define selectable configurations of the biological culture unit for: (1) loading the growth chamber; (3) transferring an aliquot from the growth chamber to the aliquot chamber via a path defined within the biological culture unit in the transfer position; and (4) extracting the aliquot from the aliquot chamber. In some embodiments the selectable positions further include (2) a growth position. In some embodiments the selectable positions further include (5) a termination position for putting a termination agent into the growth and aliquot chambers. In some embodiments the valve plate further includes a neutralizer port that is aligned with the aliquot chamber in the loading position, for loading a neutralizing agent into the aliquot chamber.

BRIEF DESCRIPTION OF THE DRAWINGS

Any quantitative dimensions shown in the drawing are to be understood as non-limiting illustrative examples. Unless otherwise indicated, the drawings are not to scale; if any aspect of the drawings is indicated as being to scale, the illustrated scale is to be understood as non-limiting illustrative example.

In FIG. 8 the transfer actuator comprises a gas coupling as in FIGS. 1 and 2.

In FIG. 9 the transfer actuator comprises a gas coupling as in FIGS. 1 and 2.

In FIG. 10 the transfer actuator comprises a plunger as in FIGS. 3 and 6, and the valve plate is in the transfer position (position #3) as in FIG. 8, again showing the third fluid path aligned to connect the first and second fluid paths in the transfer position to define the aliquot transfer path from the growth chamber to the aliquot chamber.

In FIG. 11 the transfer actuator comprises a gas coupling as in FIGS. 1 and 2.

In FIG. 12 the transfer actuator comprises a gas coupling as in FIGS. 1 and 2.

DETAILED DESCRIPTION

Figures 8, 9:
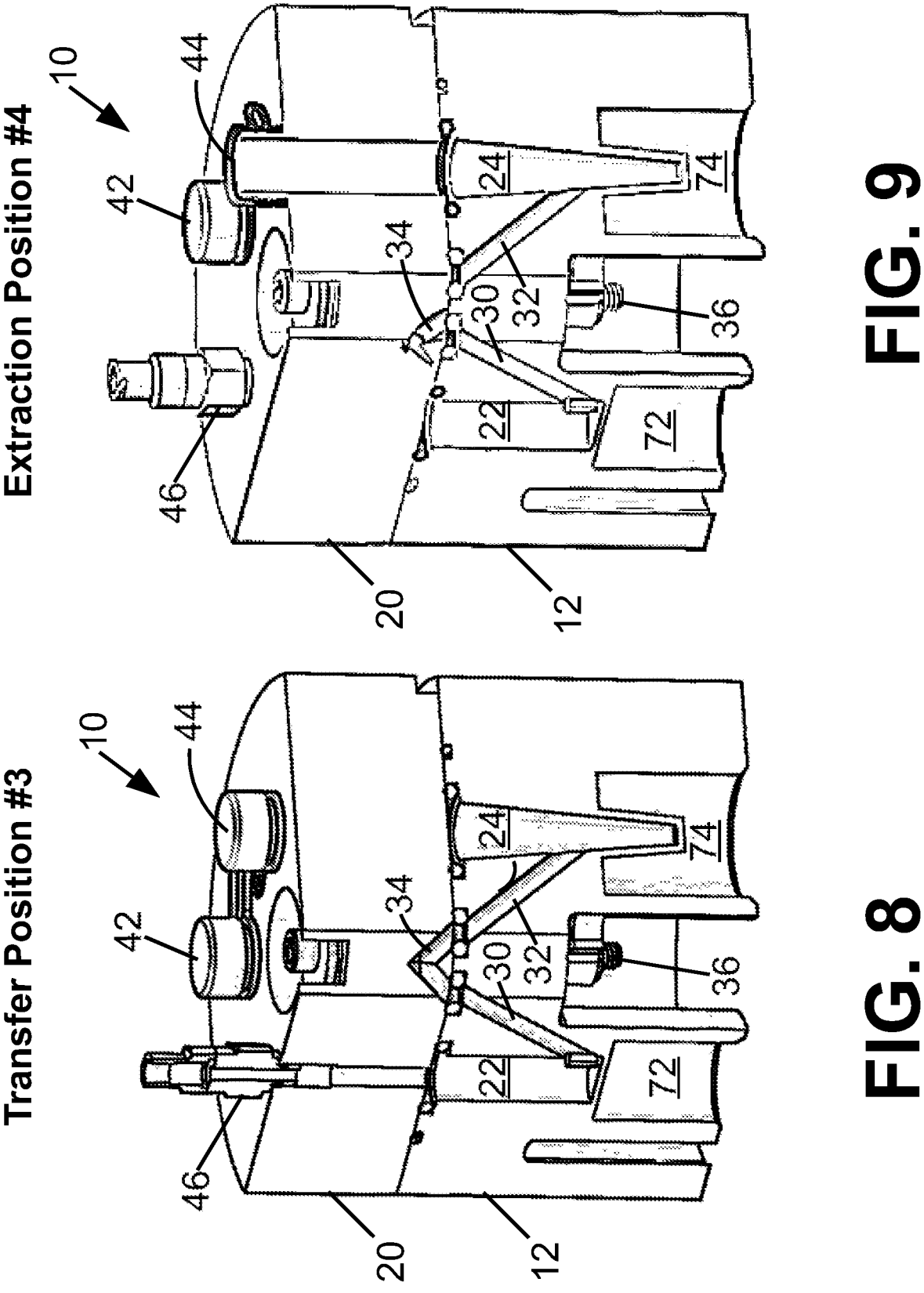
FIG. 8 diagrammatically shows a perspective sectional view of the biological culture unit with the valve plate in the transfer position (position #3), showing first, second, and third fluid paths with the third fluid path aligned to connect the first and second fluid paths in the transfer position to define an aliquot transfer path from the growth chamber to the aliquot chamber.
FIG. 9 diagrammatically shows the perspective sectional view of FIG. 8 but with the valve plate in the extraction position (position #4), showing the third fluid path not aligned to connect with the first and second fluid paths.
Figure 10:
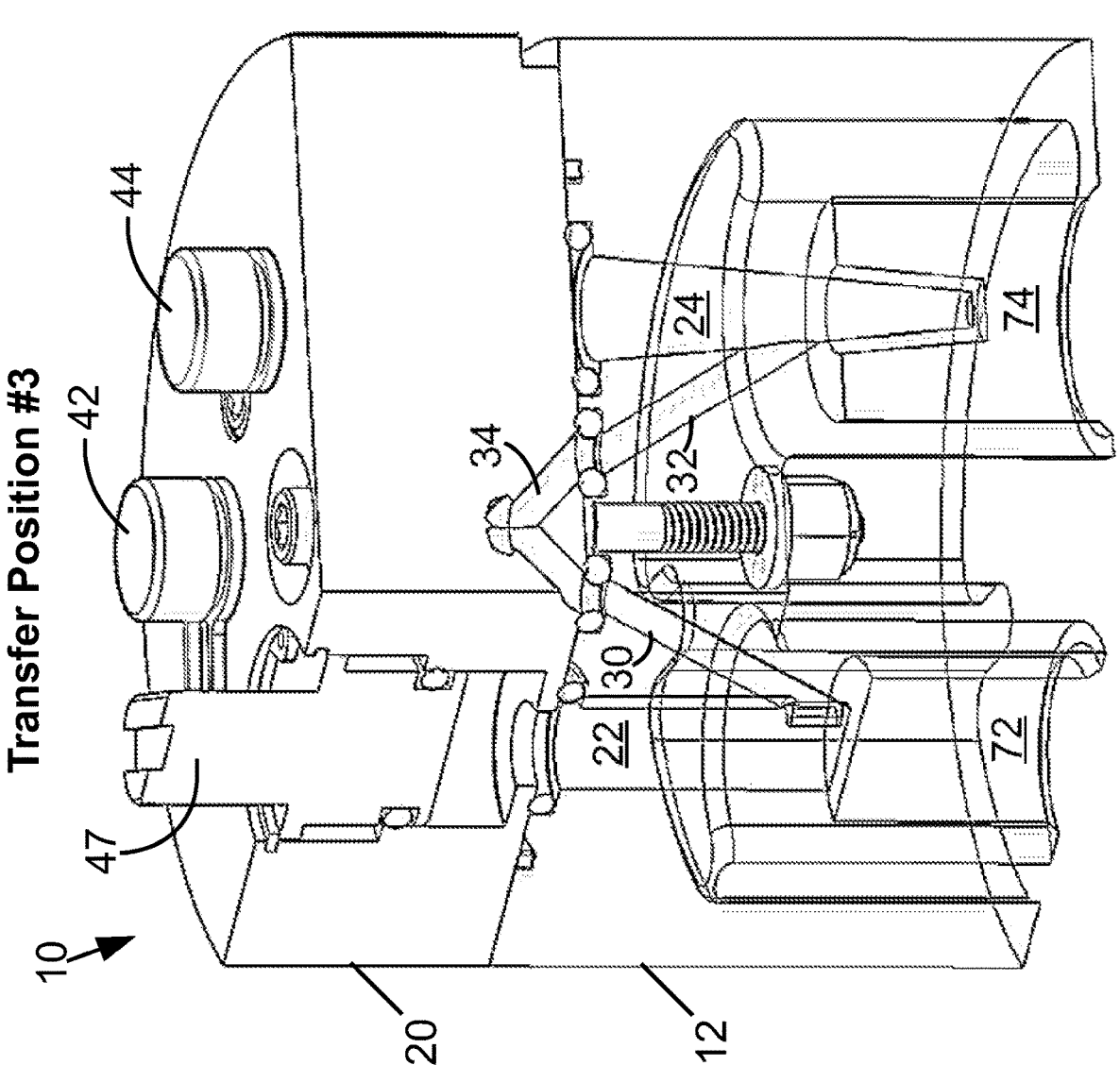
FIG. 10 shows a perspective view of the biological culture unit with the chamber body shown in transparency to reveal internal components.

With reference to FIGS. 1-12, a biological culture unit 10 includes a chamber body 12 having a top surface 14 and a bottom surface 16 (labeled only in FIG. 5), and a valve plate 20. The chamber body 12 has defined therein a growth chamber 22 having an access opening 23 at the top surface 14, and an aliquot chamber 24 having an access opening 25 at the top surface 14. As seen in FIGS. 8-10, a first fluid path 30 extends from the growth chamber 22 to the top surface 14, and similarly a second fluid path 32 extends from the aliquot chamber 24 to the top surface 14. The valve plate 20 is disposed on the top surface 14 of the chamber body 12 and is movable to define selectable configurations of the biological culture unit 10 including at least: a loading configuration in which the growth chamber 22 is accessible via the access opening 23 of the growth chamber 22 and the first and second fluid paths 30, 32 are not connected together; a transfer configuration in which the access opening 23 of the growth chamber 22 is sealed by the valve plate 20, the access opening 25 of the aliquot chamber 24 is sealed by the valve plate 20, and the first and second fluid paths 30, 32 are connected together by a third fluid path 34 defined in the valve plate 20; and an extraction position in which the aliquot chamber 24 is accessible via the access opening 25 of the aliquot chamber 24, the access opening 23 of the growth chamber 22 is sealed by the valve plate 20, and the first and second fluid paths 30, 32 are not connected together.

Figures 1, 2:
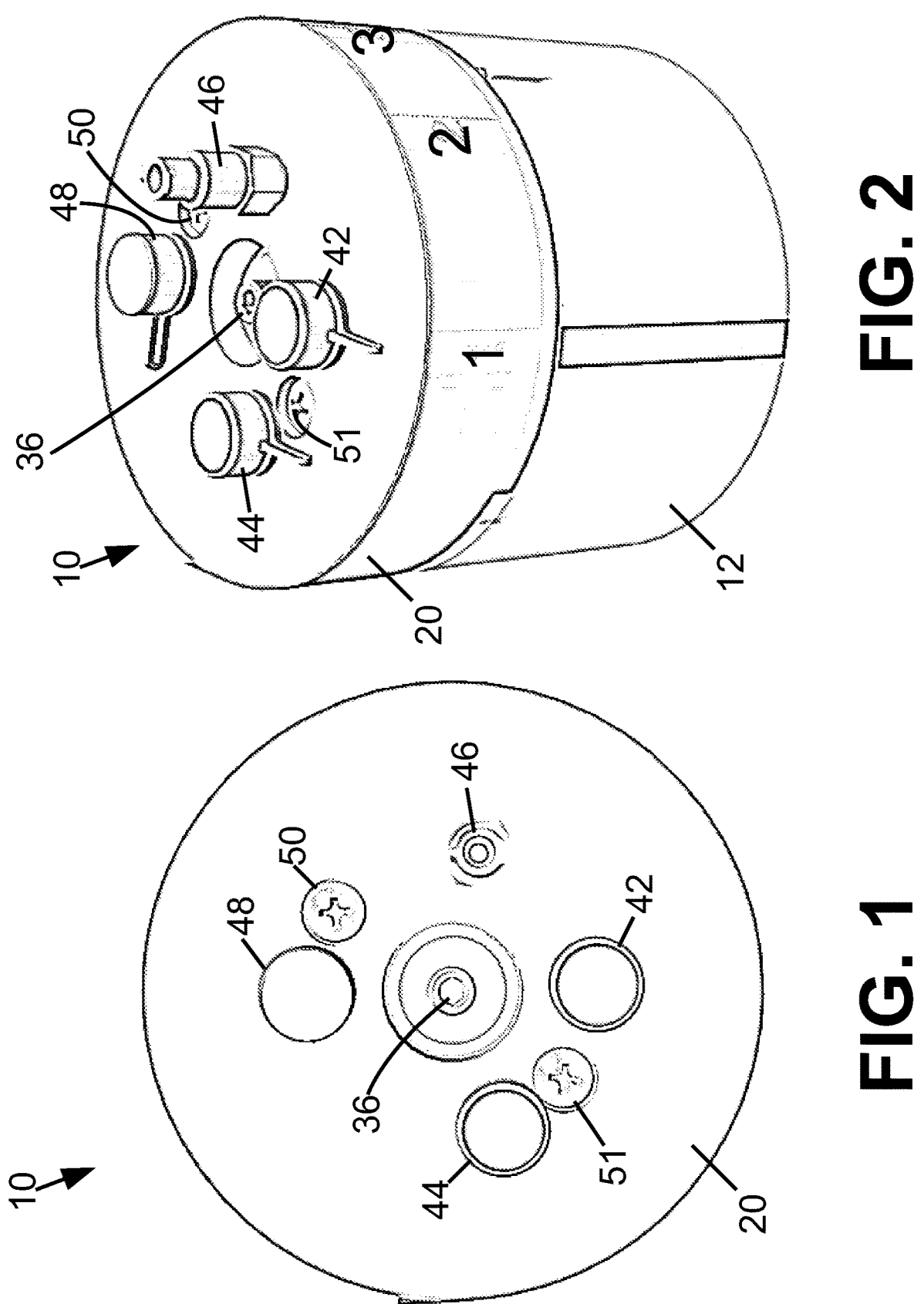
FIGS. 1 and 2 diagrammatically show top and perspective views, respectively, of a biological culture unit including a transfer actuator comprising a gas coupling.
Figure 3:
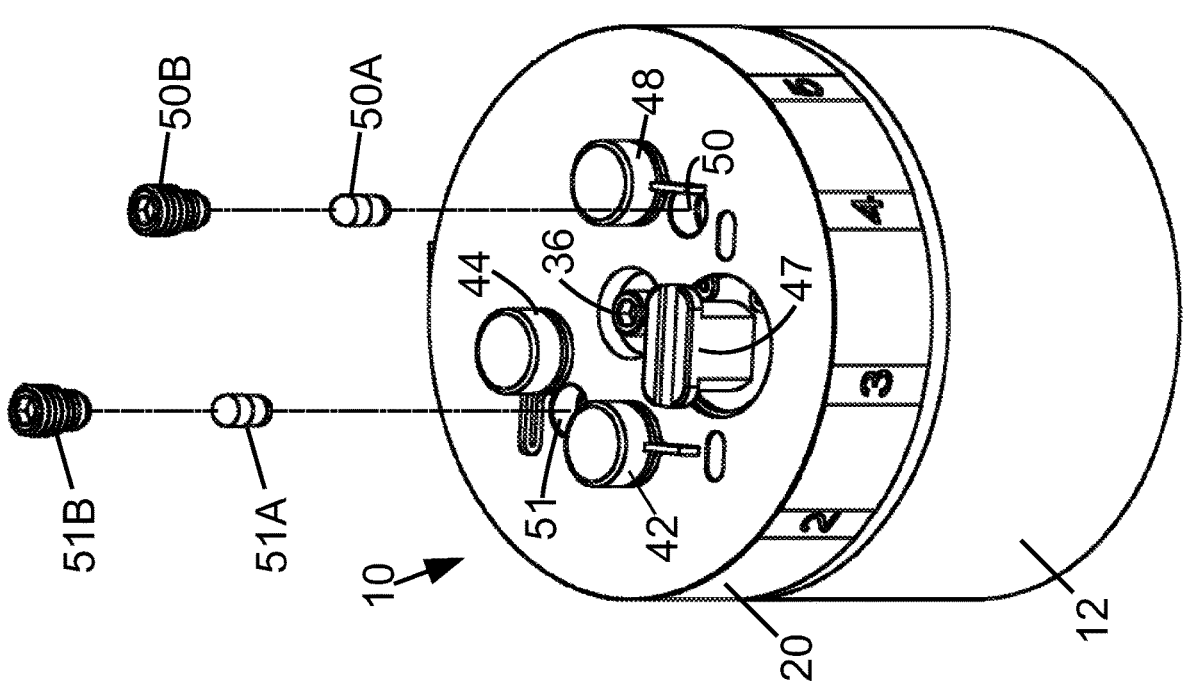
FIG. 3 diagrammatically shows a perspective view of the biological culture unit of FIGS. 1 and 2 with the loading of the termination tablets into the terminator ports diagrammatically shown, and with the transfer actuator comprising a plunger.
Figures 6, 7:
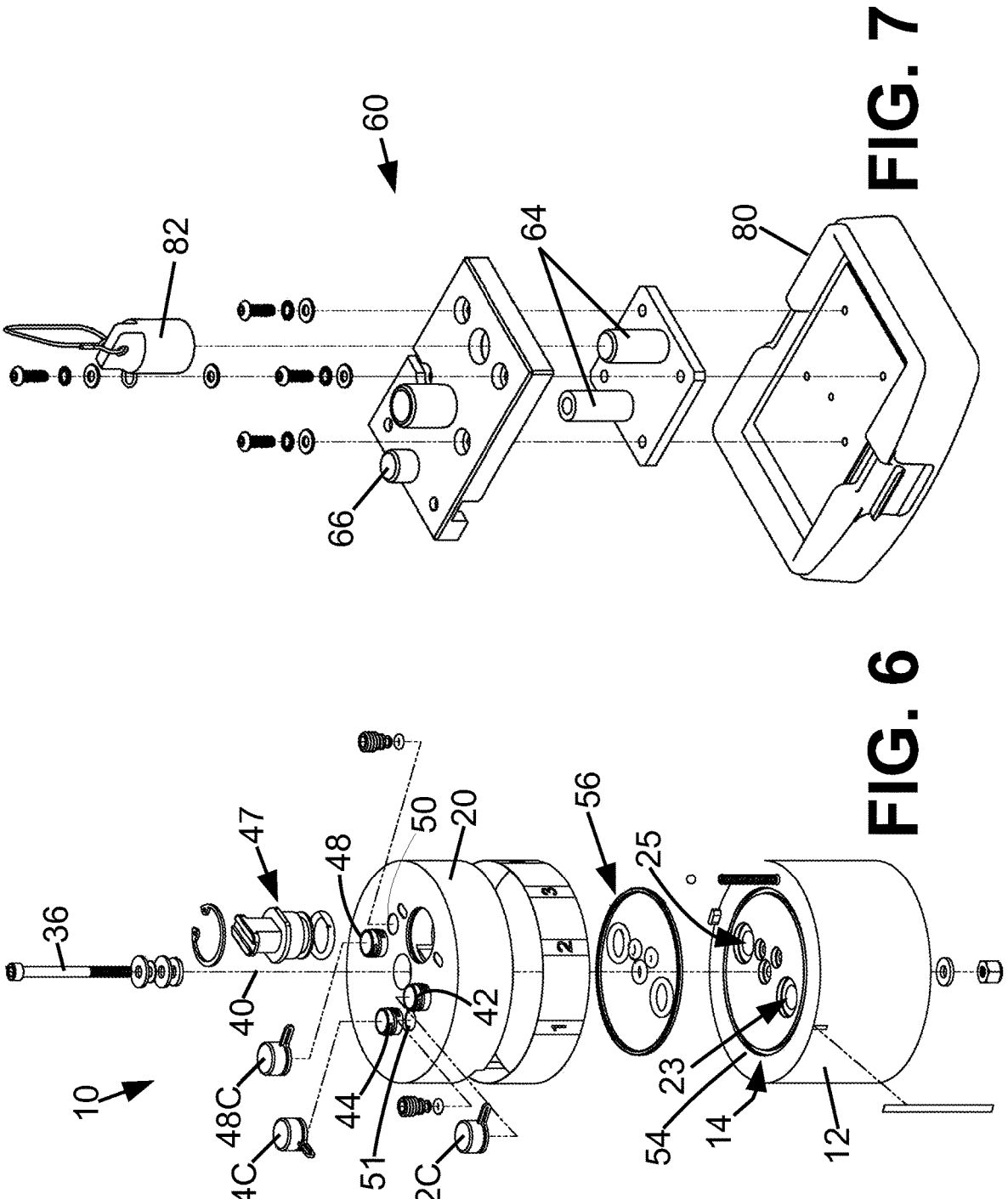
FIG. 6 diagrammatically shows an exploded perspective view of the biological culture unit, with the transfer actuator comprising a plunger per FIG. 3.
FIG. 7 diagrammatically shows an exploded perspective view of a heater adapter for mating the biological culture unit of FIGS. 1-6 with an associated temperature controller.

The illustrative valve plate 20 is disposed on the top surface 14 of the chamber body 12 and is rotatably connected (by a central bolt 36) with the chamber body 12 to rotate about a rotation axis 40 (indicated in FIGS. 5 and 6) relative to the chamber body 12. The illustrative valve plate 20 includes the aforementioned third fluid path 34 and further includes a growth chamber access port 42, an aliquot chamber access port 44, and a transfer actuator 46 comprising a gas coupling (as shown in FIGS. 1, 2, 8, 9, 11, and 12) or a transfer actuator 47 comprising a plunger (as shown in FIGS. 3, 6, and 10). Optionally, the valve plate 20 may further include a neutralizer port 48. Optionally, the valve plate 20 may further include terminator ports 50, 51. The valve plate 20 is rotatable about the rotation axis 40 into a plurality of selectable positions as set forth in Table 1. In the illustrative embodiment, starting at position #1, the valve plate 20 is rotated in a clockwise direction (when looking down on the valve plate 20, e.g. as seen in FIG. 1) to move through Positions #2, #3, #4, and #5 in that order. (In an alternative embodiment, the biological culture unit is designed to cycle through the positions #1-#5 by rotating the valve plate in the counter-clockwise direction, this being a mere reversal of parts along the rotational direction). In some embodiments, detents (not shown) are provided to stop the rotation at each successive position when it is reached. For example, the detents may be a protrusion from the top surface 14 of the chamber body that successively mates with recesses in the mating surface of the valve plate 20 aligned for each position of Table 1. As another non-limiting illustrative embodiment, the protrusion may extend from the valve plate surface and the recesses formed in the top surface 14 of the chamber body 12.

TABLE 1

| Valve Plate Positions | | |
| --- | --- | --- |
| Position | Position name | Purpose |
| #1 | Loading position | Load sample and growth medium into growth chamber; place caustic base or other neutralizing agent into neutralizer port |
| #2 | Growth position | Heat growth and aliquot chambers to grow culture |
| #3 | Transfer position | Transfer aliquot from growth chamber to aliquot chamber |
| #4 | Extraction position | Neutralize and extract aliquot |
| #5 | Termination position | Dispose termination agent into growth and aliquot chambers |

In a suitable embodiment, each of the growth chamber access port 42, the aliquot chamber access port 44, and the neutralizer port 48 may comprise a through-hole with a threaded collar that is capped by a threaded cap. The ports 42, 44, 48 are shown in the drawings with the caps on and are labeled by reference numbers 42, 44, 48; except the exploded view of FIG. 6, where the caps are shown separately and labeled as respective caps 42C, 44C, 48C. Threaded ports with threaded caps are advantageous insofar as the threaded cap can provide a reliable seal (optionally, a gasket may be disposed inside the cap to provide additional compression sealing); however, other types of port design such as pop-off caps are alternatively contemplated.

The terminator ports 50, 51 are shown in exploded view in FIG. 3. Each terminator port 50, 51 includes a respective threaded sealing bolt 50B, 51B. The terminator ports 50, 51 are shown in the drawings with the sealing bolts on and are labeled by reference numbers 50, 51; except the exploded view of FIG. 3, where the sealing bolts are shown separately and labeled as respective sealing bolts 50B, 51B. A respective termination agent 50A, 51A is loaded into the respective terminator ports 50, 51 prior to capping off with the respective sealing bolts 50B, 51B. In the illustrative example, the terminator ports 50, 51 are through-holes, such that when the valve plate 20 is rotated into the termination position (position #5) the termination agent 50A falls under gravity through the access opening 23 (which is aligned with the termination port 50 in the termination position #5) and into the growth chamber 22; and likewise the termination agent 51A falls under gravity through the access opening 25 (which is aligned with the termination port 51 in the termination position #5) and into the aliquot chamber 24. The termination agents 50A, 51A are suitably capsules or the like. In a suitable embodiment, each termination agent 50A, 51A comprises at least calcium hypochlorite or another strong bleaching or disinfectant agent.

With particular reference now to FIGS. 8 and 9, the biological culture unit 10 provides the ability to transfer an aliquot of a culture grown in the growth chamber 22 into the aliquot chamber 24 without breaking containment of either chamber 22, 24. To this end, FIG. 8 diagrammatically shows a perspective sectional view of the biological culture unit 10 with the valve plate 20 in the transfer position (position #3 of Table 1). The first fluid path 30 is defined in the chamber body 12 and has its lower end in permanent fluid connection with the growth chamber 22, typically connecting at or near the bottom of the growth chamber 22. The first fluid path 30 follows an angled upward trajectory through the chamber body 12 and terminates at an opening at the top surface 14 of the chamber body 12. In the transfer position, this opening of the first fluid path 30 at the top surface 14 of the chamber body 12 connects with an opening of the third fluid path 34 which is defined in the valve plate 20, so that in the transfer position there is a fluid path extending from the growth chamber 22 to the third fluid path 34. In analogous manner, the second fluid path 32 is defined in the chamber body 12 and has its lower end in permanent fluid connection with the aliquot chamber 24. The second fluid path 32 follows an angled upward trajectory through the chamber body 12 and also terminates at an opening at the top surface 14 of the chamber body 12. In the transfer position, this opening of the second fluid path 32 at the top surface 14 of the chamber body 12 also connects with an opening of the third fluid path 34, so that in the transfer position there is a fluid path extending from the aliquot chamber 24 to the third fluid path 34. Hence, as seen in FIG. 8 (and also in FIG. 10), in the transfer position #3 a fluid transfer path is defined from the growth chamber 22 through the first fluid path 30 through the third fluid path 34 through the second fluid path 32 and into the aliquot chamber 24.

On the other hand, after the aliquot transfer is performed, the valve plate 20 is rotated into the extraction position #4 as shown in FIG. 9. In the extraction position, the third fluid path 34 is not aligned to connect with the first fluid path 30, and the third fluid path 34 is not aligned to connect with the second fluid path 32. Consequently, the growth chamber 22 and the aliquot chamber 24 are mutually isolated in the extraction position #4. Although not specifically illustrated, the growth chamber 22 and the aliquot chamber 24 are also mutually isolated in each of the loading position #1, the growth position #2, and the termination position #5. Said another way, the first, second, and third fluid paths 30, 32, 34 are aligned to form the transfer path from the growth chamber 22 to the aliquot chamber 24 only when the valve plate 20 is in transfer position #3.

With the valve plate 20 in the transfer position #3, the transfer actuator 46, 47 is aligned with the access opening 23 of the growth chamber 22. To transfer the aliquot, the transfer actuator 46, 47 is operated to transfer the aliquot from the growth chamber to the aliquot chamber via the transfer route defined by the first fluid path 30 and the second fluid path 32 connected by the third fluid path 34. In FIGS. 1, 2, 8, 9, 11, and 12, the transfer actuator comprises a gas coupling 46. A suitable pressure source (not shown) is connected to the gas coupling and is valved open to apply pressure to transfer the aliquot. To transfer the aliquot of a known volume or mass, the applied pressure should be well-quantified. For example, the pressure source could be an air pump, syringe, or the like that applies a fixed amount of pressure for a fixed time interval to transfer the aliquot.

Figures 4, 5:
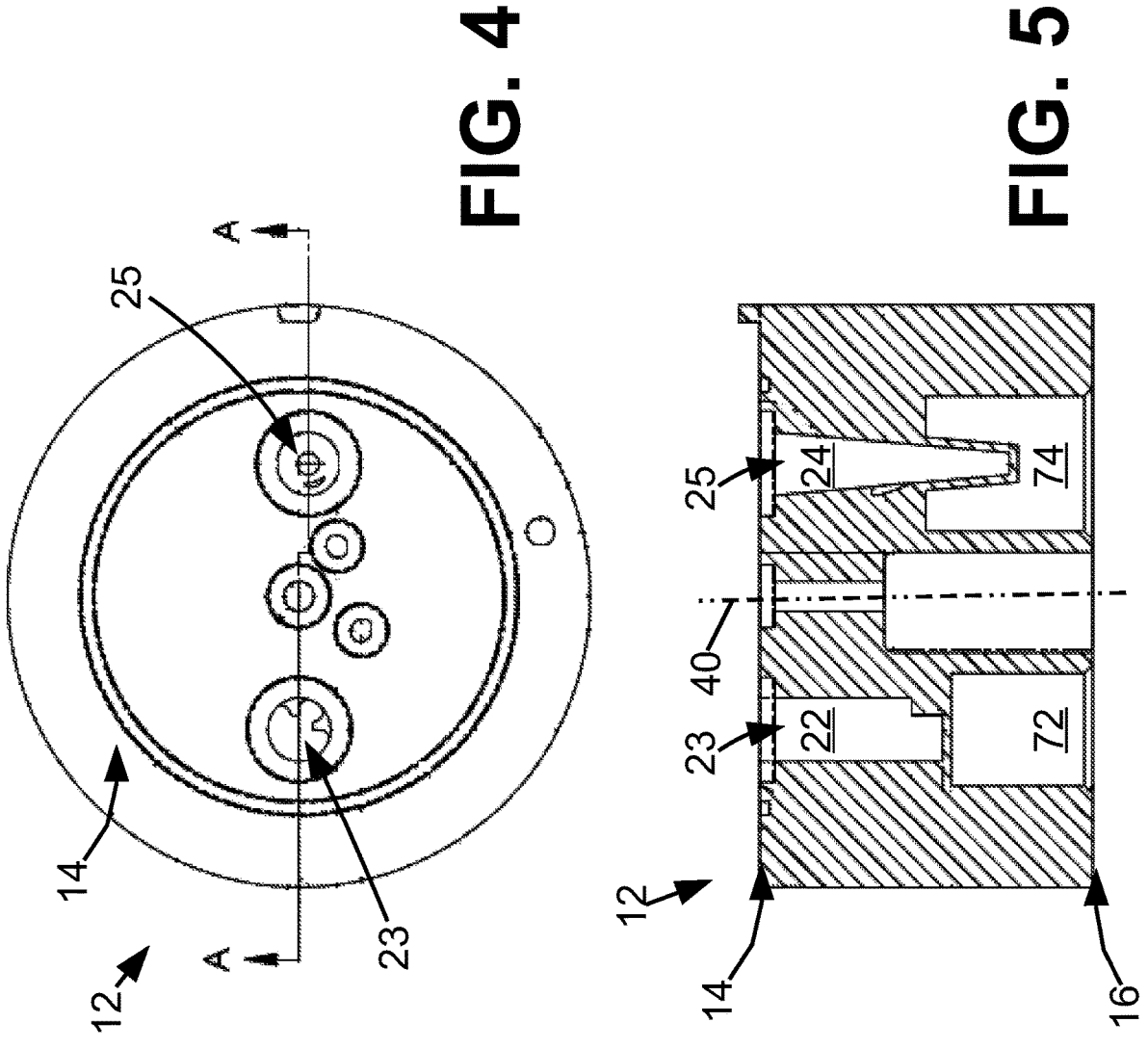
FIG. 4 diagrammatically shows a top view of the chamber body of the biological culture unit.
FIG. 5 diagrammatically shows a side sectional view of the chamber body of FIG. 4, taken along the Section A-A indicated in FIG. 4.

In FIGS. 3, 5, and 10, the transfer actuator comprises a plunger 47 that is operable when the valve plate 20 is in transfer position #3 to increase pressure in the growth chamber. The plunger 47 has certain advantages as the transfer actuator. It provides a fixed volume of air to execute the aliquot transfer, thereby ensuring a precise aliquot quantity. Furthermore, the total volume of air in the sealed volume consisting (in transfer position #3) of the growth chamber 22, aliquot chamber 24, and fluid paths 30, 32, 34 is fixed; as a consequence, when the downward force applied to the plunger 47 is released, the increased pressure produced in this fixed volume by operation of the plunger 47 automatically operates to move the plunger 47 back (at least partway) to its initial position, and in so doing tends to suction any portion of the fluid remaining in the transfer fluid paths 30, 32, 34 back into the growth chamber 22. Yet a further advantage of the plunger 47 is that it provides for the biological culture unit 10 to be a fully self-contained unit that is operable without the need to connect with an external pressure source to effectuate the aliquot transfer.

In the illustrative embodiments, the transfer actuator 46, 47 is placed on the transfer plate 20 so as to be aligned with the access opening 23 of the growth chamber 22. In this configuration, the transfer actuator 46, 47 operates to increase pressure and thereby push the aliquot from the growth chamber 22 to the aliquot chamber 24. In an alternative embodiment (not shown), it is contemplated for the transfer actuator to be placed on the transfer plate 20 so as to be aligned with the access opening 25 of the growth chamber 24. In this alternative configuration, the transfer actuator would operate to decrease pressure and thereby pull the aliquot from the growth chamber 22 into the aliquot chamber 24. For example, in this alternative configuration the transfer actuator could be a plunger that is pulled outward (i.e. away from the surface of the valve plate 20) so as to increase the volume in the piston body of the plunger and thereby decrease pressure. The benefits of the illustrative plunger 47 described herein would also be obtained in this alternative configuration, e.g. a well-defined aliquot would be transferred, the plunger would be drawn back (at least partway) to its original position after the pulling force is released, and the resulting biological culture unit would be fully self-contained.

With particular reference to FIG. 6, the top surface 14 of the chamber body 12 has a number of openings, including: the access opening 23 to the growth chamber; the access opening 25 to the aliquot chamber; the opening of the first fluid path 30 at the top surface 14; and the opening of the second fluid path 32 at the top surface 14. Additionally, the central bolt 36 passes through a through hole passing through the center of the chamber body 12, and this through hole has an opening at the top surface 14. (Instead of a through-hole, a threaded blind hole could be used with the central bolt threading into the threaded blind hole). The valve plate 20 seals these openings at the top surface 14 of the chamber body 12 except when an opening is aligned with one of the ports 42, 44, 48, or with a termination port 50, 51 (in this case, however, the seal is maintained by respective sealing bolts 50B, 51B as described with reference to FIG. 3). Additionally, in transfer position #3 the valve plate 20 seals the transfer actuator 46, 47 to the access opening 23 of the growth chamber 22. To ensure this sealing action, as seen in the exploded perspective view of FIG. 6, the top surface 14 of the chamber body 12 has defined therein an annular gasket seat around the access opening 23 of the growth chamber, an annular gasket seat around the access opening 25 of the aliquot chamber, an annular gasket seat around the opening of first fluid path 30 at the top surface 14, an annular gasket seat around the opening of second fluid path 32 at the top surface, and an annular gasket seat around the opening of the central through-hole that receives the central bolt 36. A further outer periphery annular gasket seat 54 is also defined in the top surface 14 of the chamber body 12. A set of gaskets 56 is disposed in the respective annular gasket seats to ensure proper sealing, so that the valve plate 20 operates to valve the various openings in the top surface 14 of the chamber body 12 open or closed in accordance with the various positions #1-#5.

Figures 11, 12:
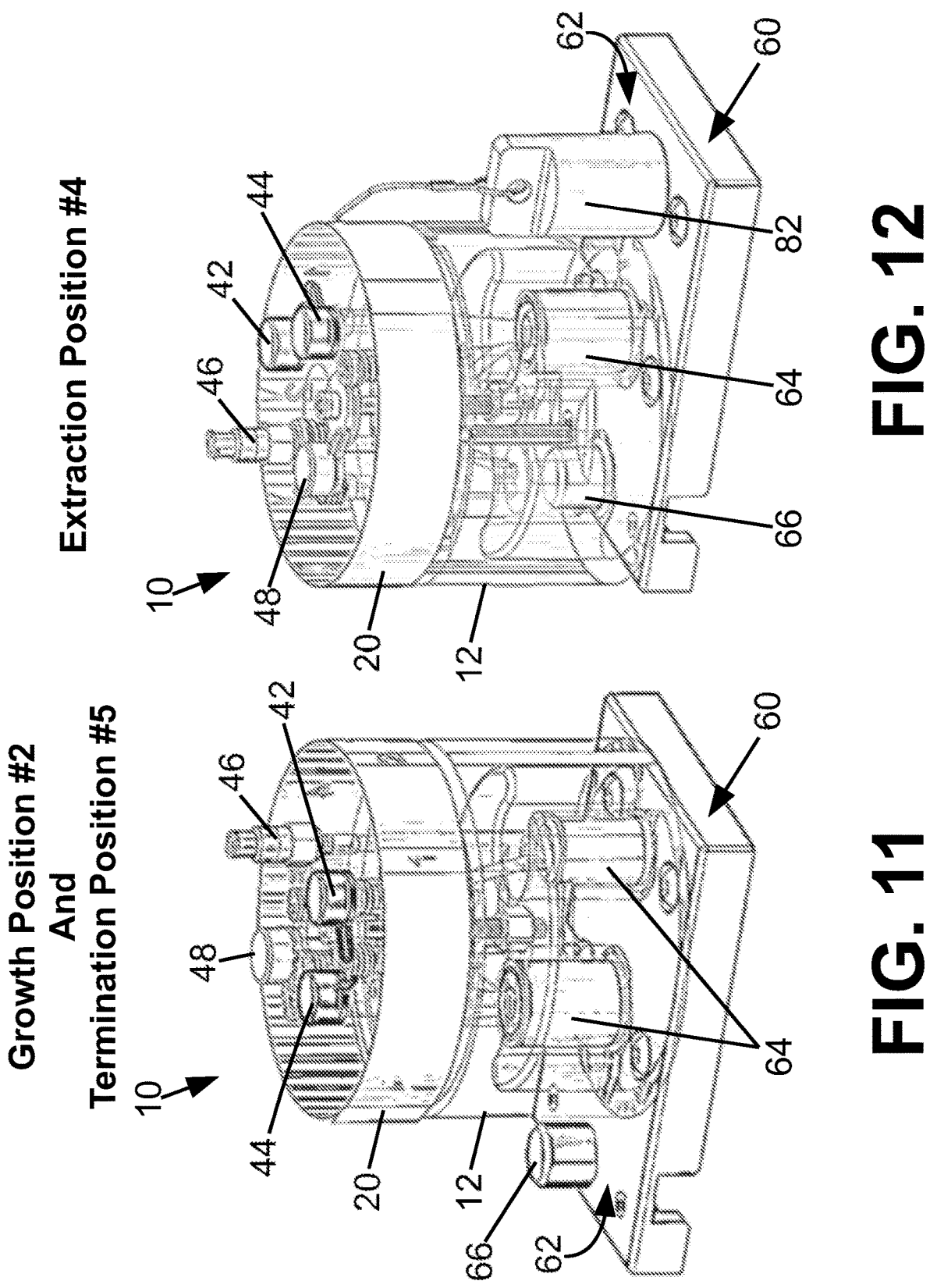
FIG. 11 shows a perspective view of the biological culture unit with the chamber body shown in transparency to reveal internal components, disposed on the heater adapter of FIG. 7, placed so as to heat both the growth chamber and the aliquot chamber.
FIG. 12 shows a perspective view of the biological culture unit with the chamber body shown in transparency, disposed on the heater adapter of FIG. 7, placed so as to heat only the aliquot chamber.

With particular reference now to FIGS. 7, 11, and 12, in the growth position #2 both the growth chamber 22 and the aliquot chamber 24 are to be heated. The heating of the growth chamber 22 in growth position #2 is designed to promote growth of the culture in the growth chamber 22, while the heating of the aliquot chamber 24 is optional but serves to promote thermal equilibrium between the growth chamber 22 and the aliquot chamber 24 during the aliquot transfer. In the extraction position #4, only the aliquot chamber 24 is to be heated, typically to a higher temperature than is applied to promote culture growth. The heating of the aliquot chamber 24 in extraction position #4 serves (along with the caustic base which was loaded into the aliquot chamber 24 via the neutralizer port 48 while in loading position #1) to neutralize (i.e. reduce the viability of) the culture in the aliquot chamber. If it is desired to retain the culture in the growth chamber 22 during neutralization of the aliquot, then the neutralization heat at transfer position #4 should be applied only to the aliquot chamber 24, and not to the growth chamber 22 (or, at least, not at a temperature high enough to neutralize the culture in the growth chamber). There can be various reasons for desiring to preserve the culture in the growth chamber 22 during neutralization and extraction of the aliquot. In one case, it may be desired to transfer additional aliquot(s) from the growth chamber to the aliquot chamber after the first aliquot transfer. In another case, if the aliquot tests positive for a pathogen then the entire biological culture unit 10 may be bagged appropriately for biological containment and shipped to a qualified laboratory for more extensive testing, e.g. to identify the precise variant of the pathogen. To provide the different types of heating for growth and aliquot neutralization, the illustrative biological culture unit is designed to mate with a heater adapter 60.

FIG. 7 shows the heater adapter 60 in exploded perspective view. FIG. 11 shows the biological culture unit 10 mated to the heater adapter 60 for culture growth in growth position #2. FIG. 12 shows the biological culture unit 10 mated to the heater adapter 60 for aliquot neutralization in extraction position #4. The illustrative heater adapter 60 has a top surface 62 including two heater posts 64 and a seating post 66 which is of lower height than the two heater posts 64. Each of the two heater posts 64 is sized and shaped to mate into either a growth chamber heater post receptacle 72 formed into the bottom surface 16 of the chamber body 12 or an aliquot chamber heater post receptacle 74 formed into the bottom surface 16 of the chamber body 12. The growth chamber and aliquot chamber heater post receptacles 72, 74 formed into the bottom surface 16 of the chamber body 12 are best seen in Section A-A shown in FIG. 5 and in FIGS. 8-10. The growth chamber heater post receptacle 72 is a blind hole formed into the bottom surface 16 of the chamber body 12 that terminates at a point close to, but not in fluid communication with, the bottom of the growth chamber 22. Similarly, the aliquot chamber heater post receptacle 74 is a blind hole formed into the bottom surface 16 of the chamber body 12 that terminates at a point close to, but not in fluid communication with, the bottom of the aliquot chamber 24. The heater adapter 60 further includes a bottom surface 80 (shown only in the exploded view of FIG. 7) that is configured to mate with an associated temperature controller (not shown). The illustrative heater adapter 60 has as its bottom surface 80 an adaptor for the Eppendorf Thermo-Stat™ C temperature controller available from Eppendorf AG (Hamburg, Germany); however, the heater adapter can be readily constructed with its bottom surface configured to mate with any particular commercially available or custom temperature controller.

With particular reference to FIG. 11, with the valve plate 20 in the growth position #2, the biological culture unit 10 is suitably placed onto the heater adapter 60 with the two heater posts 64 mating with both the growth chamber and aliquot chamber heater post receptacles 72, 74. In this way, both the growth chamber 22 and the aliquot chamber 24 are heated during the culture growth phase. The lower-height seating post 66 is not connected with the biological culture unit 10 in this arrangement.

With particular reference to FIG. 12, with the valve plate 20 in the neutralization position #4, the biological culture unit 10 is suitably placed onto the heater adapter 60 with one heater post 64 mating with the aliquot chamber heater post receptacles 74. The growth chamber heater post receptacle 72 mates with the lower-height seating post 66. In this way, only the aliquot chamber 24 is heated during the aliquot neutralization phase. The growth chamber 22 is not heated, or at most is heated to a much lower temperature compared with the aliquot chamber due to the lower height of the seating post 66. Optionally, the seating post 66 may also be made of a thermally insulating material to avoid heating the growth chamber 22. (In this case, the height of the thermally insulating seating post 66 may optionally be the same as the heights of the heater posts 64. In this arrangement, the second heater post is not coupled with the biological culture unit 10. Optionally, a thermally insulating safety cap 82 may be placed on the uncoupled heater post, as shown in FIG. 12.

It is noted that this heating arrangement described with reference to FIGS. 7, 11, and 12 is merely one contemplated approach, and numerous other arrangements for selectively applying heat to the growth and/or aliquot chamber(s) 22, 24 is contemplated. Moreover, if there is no interest in preserving the culture in the growth chamber 22 during neutralization of the aliquot in the aliquot chamber 24 then the heating arrangement can be greatly simplified—for example, with reference to FIG. 5 the two heater post receptacles 72, 74 could in this case be filled in with thermally conductive material and the bottom surface 16 of the biological culture unit 10 placed directly onto the heat plate of the associated temperature controller. Furthermore, although not illustrated, it is contemplated to include thermocouple, thermistor, or other temperature sensors to directly monitor the temperatures of the growth and aliquot chambers 22, 24. (In the absence of such temperature sensors, suitable calibration is performed to obtain the desired temperature schedule during the growth and neutralization phases).

Figure 13:
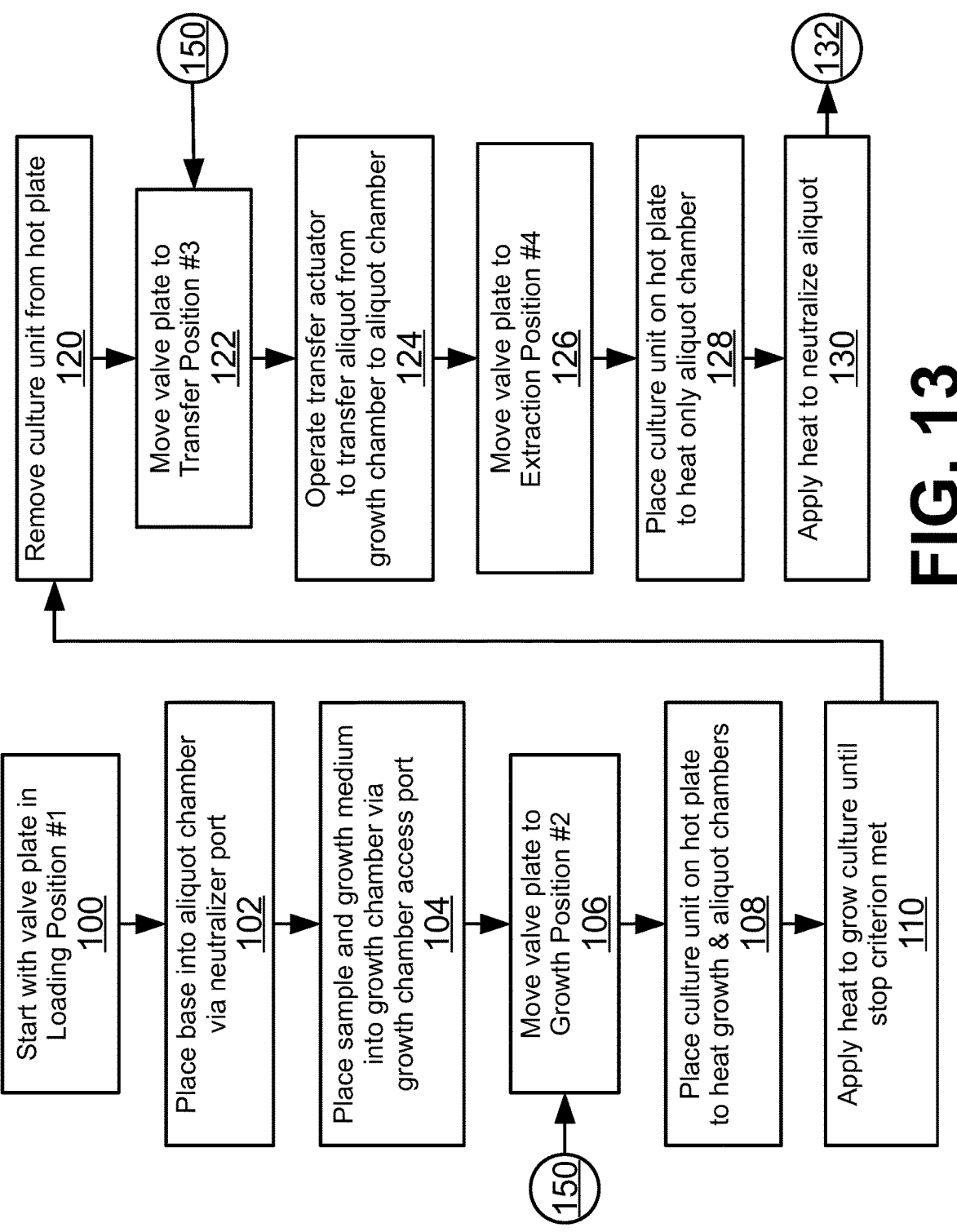
FIGS. 13 and 14 diagrammatically illustrate a biological culturing method including aliquot extraction suitably performed using the biological culture unit.
Figure 14:
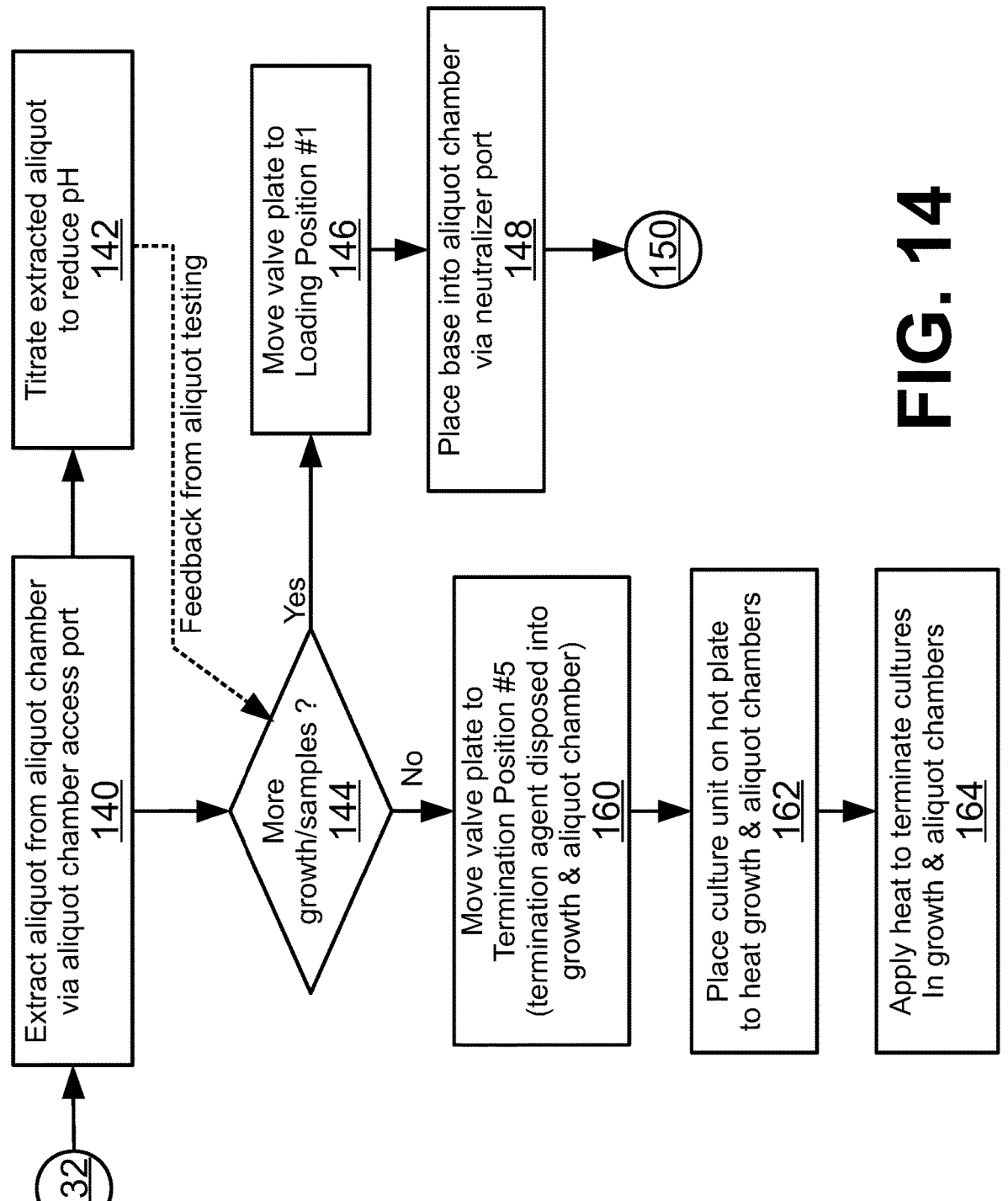

With continuing reference to FIGS. 1-12 and with further reference to FIGS. 13 and 14, an illustrative culturing process suitably performed using the biological culture unit 10 is described. The process starts at 100 with the valve plate 20 rotated into the loading position #1, in which the growth chamber access port 42 is aligned with the access opening 23 of the growth chamber 22 and the neutralizer port 48 is aligned with the access opening 25 of the aliquot chamber 24. In an operation 102, a caustic base is placed into the aliquot chamber 24 via the neutralizer port 48, and in an operation 104 the sample and the growth medium are placed into the growth chamber 22 via the growth chamber access port 42. The base is, in some embodiments, aqueous sodium hydroxide (NaOH), although other chemical bases are contemplated.

Furthermore, it is contemplated for the neutralizing agent to be a chemical other than a base. The growth medium is chosen for the specific type of pathogen which is the target of the culturing. For many pathogens, a standard brain heart infusion broth (BHIB) growth medium is suitable. The sample may be a swab taken from inside the mouth of a person or animal suspected of being infected by the pathogen, or a swab of a surface in the case of a pathogen that is communicable by surface transmission pathways, or any other appropriate sample that may be credibly expected to possibly contain the pathogen which is the target of the culturing.

In a variant embodiment, the neutralizer port 48 is omitted, and the base is placed into the aliquot chamber 24 via the aliquot chamber access port 44 with the valve plate rotated into position #4 before rotating the valve plate to position #1.

Although not shown in FIGS. 13 and 14, during the loading phase with the valve plate 20 in loading position #1 as per 100, the respective termination agent 50A, 51A is loaded into the respective terminator ports 50, 51 prior to capping off with the respective sealing bolts 50B, 51B, as diagrammatically illustrated in FIG. 3. In one suitable embodiment, the terminator agent is suitably at least 50 mg of active chlorine equivalents in the form of calcium hypochlorite, i.e. $Ca(OCl)_2$, although other termination agents are contemplated (e.g. quaternary ammonium compounds).

With the base loaded into the aliquot chamber 24 and the sample and growth medium loaded into the growth chamber 22, at an operation 106 the valve plate 20 is moved to the growth position #2. At an operation 108 the biological culture unit is placed onto the hot plate (e.g., using the heater adapter 60), e.g. as shown in FIG. 11. In an operation 110, the associated temperature controller is operated to apply heat to grow the culture in the growth chamber 22. The temperature setting of the associated temperature controller may be set by calibration runs, e.g. controlled based on a built-in temperature sensor of the associated temperature controller. Alternatively, if a temperature sensor is provided in the chamber body to more precisely measure the growth chamber temperature then this temperature sensor signal can be input to the associated temperature controller to provide more precise temperature control. The heating operation 110 is continued until some stop criterion is met. In some culture processes, the stop criterion is visually observed turbidity (i.e., cloudiness or haziness) of the liquid in the growth chamber 22. For this approach, the chamber body 12 should be made of a transparent or translucent material. In one actually-constructed embodiment, the chamber body 12 was made of a clear polycarbonate material, while the valve assembly 20 was made of a polysulfone material, but this is merely a non-limiting illustrative example. In other embodiments, it is contemplated to program the associated temperature controller to execute a pre-programmed temperature-versus-time schedule that has been calibrated to provide a desired amount of culture growth. Other manual or automated stop criteria are contemplated, such as a color change induced by the growing culture (manually observed or automatically detected using a suitable optical sensor), stopping when the growth chamber reaches a certain pressure (assuming the growing culture is expelling a gas, and further assuming the growth chamber is provisioned with a pressure sensor, not shown), various combinations thereof, and/or so forth.

With continuing reference to FIG. 13, upon the stop criterion being reached the biological culture unit 10 is removed from the associated temperature controller. (Alternatively, it can be kept on the temperature controller and the temperature controller merely turned off to stop applying heat). In an operation 122, the valve plate 20 is rotated to the transfer position #3 as shown in FIG. 8 (for the transfer actuator comprising the gas coupling 46) or FIG. 10 (for the transfer actuator comprising the plunger 47). In an operation 124, the transfer actuator 46, 47 is operated to transfer an aliquot of the culture from the growth chamber 22 to the aliquot chamber 24 via the transfer fluid path formed in the transfer position by the first, second, and third fluid paths 30, 32, 34. After the aliquot transfer is completed, in an operation 126 the valve plate 20 is moved to the extraction position #4, and in an operation 128 the biological culture unit 10 is placed back onto the hot plate of the associated temperature controller, in the neutralization arrangement as shown in FIG. 9. In an operation 130, the associated temperature controller is operated to heat the aliquot chamber 24 to neutralize the aliquot. This neutralization process entails a combination of the base (placed into the aliquot chamber 24 at operation 102) and the applied heat. In one suitable approach, the base is aqueous NaOH mixed with the aliquot to a final concentration of 0.1N, and then heated at 100° C. for 60 minutes. However, other neutralization processes are contemplated, with the specific neutralization process being suitably chosen for the suspected pathogen under test. It should be noted that the neutralization does not necessarily achieve complete sterilization of the aliquot—rather, in general it is sufficient to neutralize the aliquot of the culture to a level of bioactivity that is commensurate with the expected level of bioactivity of the sample that was placed into the growth chamber 22 at operation 104. In this way, the beneficial effect of biological amplification by way of the culturing is achieved without increasing the biohazard above that presented by handling the original sample. This means that the beneficial effect of biological amplification is achieved without a concomitant increase in risk of infection to persons handling the sample and culture. Further, the illustrative approach employing 0.1N NaOH at 100° C. is believed to provide beneficial release of predominantly intact nucleic acids from the cultured biological sample, so that subsequent pathogen testing is further facilitated, and the likelihood of a successful pathogen detection event is greatly increased after biological amplification in the biological culture unit 10.

The connector 132 shown in FIGS. 13 and 14 indicates process flow transfer from the neutralization operation 130 to an aliquot extraction operation 140 indicated in FIG. 14. With the valve plate 20 still in the extraction position #4 as set in operation 126, the aliquot chamber access port 44 is aligned with the access opening 25 of the aliquot chamber 24, and so the aliquot can be extracted via the aliquot chamber access port 44. Preferably, in an operation 142 the extracted aliquot is titrated with an acid to reduce the high pH caused by the base, e.g. 0.1N acid should be effective to reduce the illustrative 0.1N NaOH/aliquot solution to near-neutral pH. The extracted aliquot after acid titration is then tested (not shown) using any suitable test procedures suitable for detecting and/or characterizing the suspected pathogen. As such tests are being done in the field in some contemplated applications of the biological culture unit 10, the tests may not be as sophisticated as what might be performed at an advanced laboratory; however, the tests are beneficial if they can identify whether the culture contains the suspected pathogen with reasonable accuracy. During the testing, the biological culture unit 10 is suitably kept at refrigeration temperature to keep the culture substantially in stasis.

If the biological culture unit is intended to allow for multiple aliquots to be extracted, then in a decision 144 it is determined whether more culture growth is desired and/or more aliquots are to be extracted. This decision 144 may be based on feedback from the testing of the already-extracted aliquot. For example, if the testing is inconclusive as to whether the suspected pathogen is present, then additional culture growth might be desired to provide further biological amplification in order to hopefully obtain a more conclusive result. In another possible scenario, if the initial aliquot tests positive for the suspected pathogen then a second aliquot may be extracted to send to a more advanced laboratory to perform variant identification and/or other further testing. If additional aliquot(s) are to be drawn, then in an operation 146 the valve plate 20 is moved back to the loading position #1. In so doing, consideration must be taken as regards passing through the termination position #5, since passing through termination position #5 would result in the termination agents 50A, 50B dropping into the growth and aliquot chambers 22, 24. (See FIG. 3 and related discussion). If the valve plate 20 can be moved bidirectionally (e.g., in the illustrative examples clockwise to cycle through positions #1, #2, #3, #4, #5 in that order; or counter-clockwise to move through positions #4, #3, #2, #1 in that order, then the operation 146 can avoid termination position #5 by rotating the valve plate 20 counterclockwise from extraction position #4 and passing through transfer position #3 and growth position #2 to reach loading position #1. In another embodiment, if the valve plate 20 is designed to rotate in only one direction (e.g., in the illustrative examples clockwise to cycle through positions #1, #2, #3, #4, #5 in that order) then multiple aliquot extractions can be provided for by modifying the terminator ports 50, 51 to require an affirmative user action (beyond rotating the valve plate 20 to the termination position #5) to release the termination agents 50A, 50A. For example, a sealed push-button (not shown) can be incorporated into the sealing bolts 50B, 51B so that the termination agents 50A, 50A are only released into the growth and aliquot chambers 22, 24 upon both the valve plate being in the termination position #5 and the push buttons being pressed. In either case, after rotating the valve plate 20 into the loading position #1 via operation 146, base is placed into the aliquot chamber 24 via the neutralizer port 48. Process flow then follows connector 150 to return process flow to operation 106 of FIG. 13 to continue culture growth. Alternatively, if no further culture growth is desired then then the connector 150 suitably returns process flow to operation 122 to initiate the next aliquot transfer.

With continuing reference particularly to FIG. 14, if on the other hand the decision 144 is that no further aliquots are needed (or, alternatively, if the biological culture unit is intended to be single-use with no consideration being given to extracting more than one aliquot), then in an operation 160 the valve plate is moved to the termination position #5. Because the terminator ports 50, 51 comprise through-holes, moving the valve plate 20 to termination position #5 automatically drops the termination agents 50A, 51A into the growth and aliquot chambers 22, 24. (Alternatively, if pressing a push-button or other affirmative action is required to drop the termination agents as in a previously discussed alternative approach, then the operation 160 suitably further includes pushing the push-button to drop the termination agents 50A, 51A into the growth and aliquot chambers 22, 24.) In an operation 162, the biological culture unit 10 is placed onto the associated temperature controller, in the arrangement shown in FIG. 11 so as to apply heat to both the growth and aliquot chambers 22, 24. In an operation 164, the associated temperature controller is operated to apply sufficient heat to the growth and aliquot chambers 22, 24 to cause the termination agents 50A, 51A to neutralize or (more preferably) sterilize the growth and aliquot chambers 22, 24. For the illustrative example of the terminator agent being at least 50 mg of active chlorine equivalents in the form of calcium hypochlorite, i.e. $Ca(OCl)_2$, heating at 100° C. for at 20 minutes is expected to be sufficient to achieve termination of viability. Again, this is merely an illustrative example, and higher temperature and/or incubation time is contemplated to achieve termination depending upon the dose of terminator agent, the sizes of the chambers 22, 24, and/or other factors.

The preferred embodiments have been illustrated and described. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A biological culture unit, comprising:
a chamber body having defined therein a growth chamber and an aliquot chamber; and
a valve plate disposed on a top surface of the chamber body and connected to the top surface of the chamber body via a central bolt defining a rotation axis, the valve plate being rotatable about the rotation axis to define selectable configurations of the biological culture unit for:
loading the growth chamber; and transferring an aliquot from the growth chamber to the aliquot chamber via a path defined in the valve plate in a transfer position.

2. The biological culture unit of claim 1, wherein the valve plate is rotatable about the rotation axis to define a further selectable configuration that includes an extraction position for extracting the aliquot from the aliquot chamber.

3. The biological culture unit of claim 1, wherein the valve plate is rotatable about the rotation axis to define a further selectable configuration that includes a growth position that separates the growth chamber and the aliquot chamber.

4. The biological culture unit of claim 1, wherein the valve plate further includes a neutralizer port that is aligned with the aliquot chamber, the neutralizer port being configured to load a neutralizing agent into the aliquot chamber when the valve plate is in the selectable configuration for loading the growth chamber.

5. The biological culture unit of claim 1, wherein the valve plate further includes first and second terminator ports and the valve plate is rotatable about the rotation axis to define further selectable configurations that include a termination position in which the first terminator port is aligned with the access opening of the growth chamber and the second terminator port is aligned with the access opening of the aliquot chamber.

6. The biological culture unit of claim 1, wherein, in the transfer position, a transfer actuator is aligned with an access opening of the growth chamber.

7. The biological culture unit of claim 6, wherein the transfer actuator comprises a plunger that is operable when the valve plate is in the transfer position to increase pressure in the growth chamber; or
wherein the transfer actuator comprises a gas coupling.

8. The biological culture unit of claim 1, wherein:
a top surface of the chamber body has defined therein an annular gasket seat around an access opening of the growth chamber, an annular gasket seat around an access opening of the aliquot chamber, an annular gasket seat around an opening of a first fluid path at the top surface, and an annular gasket seat around an opening of a second fluid path at the top surface; and
gaskets disposed in the respective annular gasket seats.

9. The biological culture unit of claim 1, wherein a bottom surface of the chamber body has formed therein a growth chamber heater post receptacle aligned with the growth chamber and an aliquot chamber heater post receptacle aligned with the aliquot chamber.

10. The biological culture unit of claim 9, further comprising:
a heater adapter having a top surface including two heater posts, each sized and shaped to mate into either the growth chamber heater post receptacle or the aliquot chamber heater post receptacle, and further having a bottom surface configured to mate with an associated temperature controller.

11. A biological culture unit, comprising:
a chamber body having defined therein a growth chamber and an aliquot chamber; and
a valve plate connected to the chamber body via a central bolt defining an axis, the valve plate movable about the axis to define selectable configurations of the biological culture unit for:
loading the growth chamber; and
transferring an aliquot from the growth chamber to the aliquot chamber via a path defined in the valve plate in a transfer position.

12. The biological culture unit of claim 11, wherein the central bolt defines a rotation axis about which the valve plate is rotatable.

13. The biological culture unit of claim 11, wherein the axis is a rotatable axis, and the valve plate is rotatable about the rotation axis relative to the chamber body.

14. The biological culture unit of claim 11, wherein the valve plate is movable about the axis to further define selectable configurations including:

an extraction position for extracting the aliquot from the aliquot chamber; or a growth position that separates the growth chamber and the aliquot chamber.

15. The biological culture unit of claim 11, wherein the valve plate further includes a neutralizer port that is aligned with the aliquot chamber, the neutralizer port being configured to load a neutralizing agent into the aliquot chamber when the valve plate is in the selectable configuration for loading the growth chamber.

16. The biological culture unit of claim 11, wherein the valve plate further includes first and second terminator ports and the valve plate is rotatable about the rotation axis to define further selectable configurations that include a termination position in which the first terminator port is aligned with the access opening of the growth chamber and the second terminator port is aligned with the access opening of the aliquot chamber.

17. The biological culture unit of claim 11, wherein, in the transfer position, a transfer actuator is aligned with an access opening of the growth chamber.

18. The biological culture unit of claim 17, wherein the transfer actuator comprises a plunger that is operable when the valve plate is in the transfer position to increase pressure in the growth chamber; or wherein the transfer actuator comprises a gas coupling.

19. The biological culture unit of claim 11, wherein a bottom surface of the chamber body has formed therein a growth chamber heater post receptacle aligned with the growth chamber and an aliquot chamber heater post receptacle aligned with the aliquot chamber.

20. The biological culture unit of claim 19, further comprising:

a heater adapter having a top surface including two heater posts, each sized and shaped to mate into either the growth chamber heater post receptacle or the aliquot chamber heater post receptacle, and further having a bottom surface configured to mate with an associated temperature controller.

* * * * *